US007704942B2

(12) United States Patent
Goeke

(10) Patent No.: US 7,704,942 B2
(45) Date of Patent: Apr. 27, 2010

(54) FRAGRANCE AND FLAVOUR COMPOSITIONS

(75) Inventor: Andreas Goeke, Duebendorf (CH)

(73) Assignee: Givaudan SA, Vernier (CH)

( * ) Notice: Subject to any disclaimer, the term of this patent is extended or adjusted under 35 U.S.C. 154(b) by 790 days.

(21) Appl. No.: 10/481,733

(22) PCT Filed: Jun. 28, 2002

(86) PCT No.: PCT/CH02/00352

§ 371 (c)(1),
(2), (4) Date: Jun. 14, 2004

(87) PCT Pub. No.: WO03/002084

PCT Pub. Date: Jan. 9, 2003

(65) Prior Publication Data

US 2005/0042255 A1 Feb. 24, 2005

(30) Foreign Application Priority Data

Jun. 30, 2001 (EP) .................................. 01115991

(51) Int. Cl.
*A61K 8/18* (2006.01)

(52) U.S. Cl. ........................................................ 512/19

(58) Field of Classification Search ...................... 512/1
See application file for complete search history.

(56) References Cited

U.S. PATENT DOCUMENTS

| | | | | |
|---|---|---|---|---|
| 4,190,591 | A | 2/1980 | Kaiser et al. | 260/347.8 |
| 4,292,210 | A | 9/1981 | Blume et al. | |
| 4,306,096 | A | 12/1981 | Kiwala et al. | |
| 4,396,523 | A | 8/1983 | Blume et al. | |
| 4,650,604 | A | 3/1987 | Broekhof et al. | |
| 4,657,700 | A | 4/1987 | Ochsner | |
| 4,696,766 | A * | 9/1987 | Naipawer | 512/8 |
| 4,904,465 | A | 2/1990 | Maillefer | 424/70 |
| 5,169,669 | A * | 12/1992 | Haynes et al. | 426/607 |
| 5,244,893 | A * | 9/1993 | Elbe et al. | 514/217.03 |
| 5,707,961 | A | 1/1998 | Bajgrowicz et al. | 512/17 |
| 6,069,125 | A * | 5/2000 | Pesaro | 512/10 |
| 6,194,362 | B1 * | 2/2001 | Trinh et al. | 510/101 |
| 6,319,889 | B1 | 11/2001 | Lenselink et al. | |
| 6,339,146 | B1 * | 1/2002 | Ogawa et al. | 536/4.1 |
| 6,426,365 | B1 * | 7/2002 | Shinkai et al. | 514/513 |
| 6,686,336 | B2 * | 2/2004 | Nagasawa | 514/19 |
| 2005/0049146 | A1 * | 3/2005 | Chiarello et al. | 504/218 |

FOREIGN PATENT DOCUMENTS

| | | | | |
|---|---|---|---|---|
| CH | 632 753 | A5 | 10/1982 | |
| EP | 0071182 | A2 | 2/1983 | |
| EP | 0 334 005 | | 9/1989 | |
| EP | 0 976 708 | A1 | 2/2000 | |
| EP | 1 269 982 | A1 | 1/2003 | |
| JP | 51106748 | | 9/1976 | |
| JP | 58021634 | * | 2/1983 | 568/721 |
| JP | 61043106 | | 3/1986 | |
| JP | 61103819 | | 5/1986 | |
| JP | 6097932 | | 4/1994 | |
| JP | 06287591 | | 10/1994 | |
| JP | 07291883 | | 11/1995 | |
| JP | 2000044506 | | 2/2000 | |

OTHER PUBLICATIONS

Mihara, S.; Shibamoto, T. J. Agric. Food. Chem. 1982, 30, 1215-1218.*
International Search Report for PCT/CH02/00352.*
Rossiter, K. "Structure-Odor Relationship.s " Chem. Reviews, 1996, 96, 3201-3240.*
PCT International Search Report for PCT/CH02/00352 dated Apr. 16, 2003.
Patent Abstracts for Japan vol. 007 No. 095 (C-163, Aug. 23, 1983 -& JP 58 021634 A (Ogawa Kouriyou KK), Feb. 8, 1983.
J Agric, Food Chem. 1982, 30, 1215-1218.
Principles and Some Techniques of High-Resolution Headspace Analysis Andrew Dravnieks* and Anne O'Donnell, J. Agri. Food. Chem., 1971, 19, 6, pp. 1049-1056.
Organometallics, 1989, vol. 8, No. 1, p. 132-140.
English language abstract for JP61043106 obtained online from the European Patent Office web site, esp@cenet, Date: Mar. 1, 1986.
English language abstract for EP0071182 (a correspondent of JP58024513) obtained online from the European Patent Office web site, esp@cenet, Date: Feb. 14, 1983.
English language abstract for JP6287591 obtained online from the European Patent Office web site, esp@cenet, Date: Oct. 11, 1994.
English language abstract for JP7291883 obtained online from the European Patent Office website, esp@cenet, Date: Nov. 7, 1995.

* cited by examiner

*Primary Examiner*—Walter D Griffin
*Assistant Examiner*—Bobby Ramdhanie
(74) *Attorney, Agent, or Firm*—Norris McLaughlin & Marcus, PA

(57) ABSTRACT

The invention relates to phenyl-cycloalkanes of formula (I) wherein the groups $R^1$ to $R^6$ are defined in the specification.

(I)

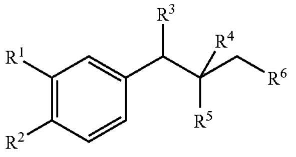

4 Claims, No Drawings

FRAGRANCE AND FLAVOUR COMPOSITIONS

This invention relates to aryl-cycloalkanes, in particular phenyl-cycloalkanes, having spicy and anisic odour notes and to flavour and fragrance compositions containing one or more of the compounds.

Compounds having spicy and anisic odour notes are of interest in the flavour and fragrance industry.

However, certain molecules, e.g. eugenol and anethole, despite having these interesting odour notes are perceived as being disadvantageous, e.g. they show a propensity towards discolouration upon storage, and therefore their use becomes limited to certain applications.

Structural modification of these molecules however, either result in a failure to retain the spicy and anisic odourant properties or the odourant properties are retained but they are far less intense and rich.

Thus, in the Journal of Agric. Food Chem., Vol. 30, No. 6, 1215-1218, the propenyl side-chain of eugenol and certain related compounds is converted to a cyclopropyl group. These cyclopropyl-substituted compounds are described as having spicy and floral properties and it is speculated that they may find use as flavourant.

In EP 334005 hydrogenation of the aromatic ring of eugenol gave 2-methoxy-4-propyl-1-cyclohexanol which was described as having green, parsley-like odourant properties.

Finally, the propenyl group of eugenol and anethole was converted to the propyl group to give dihydro-eugenol and 4-propyl-anisol. However, these molecules were less strong than their propenyl substituted counterpart (S. Arctander, Perfume and Flavor Chemicals, 1982).

Accordingly, there remains a need to provide molecules that do not possess the disadvantages of the prior art molecules but which retain their spicy and anisic odour notes and are diffusive and substantive.

It has now be found that certain compounds can be developed that are stable to discolouration and yet are substantive, diffusive and possess the desirable spicy and anisic odour notes.

Accordingly, the invention provides in one of its aspects a flavour or fragrance composition comprising a compound of formula (I)

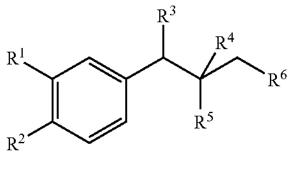

wherein, $R^1$ is hydrogen, OH, or alkoxy having 1 to 3 carbon atoms, $R^2$ is hydrogen, OH, or alkoxy having 1 to 3 carbon atoms, with the proviso that compounds of formula (I), wherein $R^1$ and $R^2$ are both hydrogen are excluded, or $R^1$ and $R^2$ taken together is a divalent radical —O—$CH_2$—O—, $R^3$ is hydrogen, or —$CH_3$, $R^4$ is hydrogen, or —$CH_3$, or $R^3$ and $R^4$ taken together is a divalent radical $(CH_2)_n$, $C(CH_3)_2$, or $CH(CH_3)$ which forms a cycloalkane ring together with the carbon atoms to which it is attached, $R^5$ is hydrogen, or —$CH_3$, $R^6$ is hydrogen, or —$CH_3$, or $R^5$ and $R^6$ taken together is a divalent radical $(CH_2)_n$, $(CH_2)_{n-1}CH(CH_3)$, or $(CH_2)_{n-1}C(CH_3)_2$ which forms a cycloalkane ring together with the carbon atoms to which it is attached, n is an integer 1, 2, or 3, and wherein at least one cycloalkane ring is present.

Compounds of the formula (I) employed in a composition according to the invention show good diffusion and high substantivity, leading to persistence of odour. For example, 1-cyclopropylmethyl-4-methoxy-benzene has an olfactometer odour threshold value 80 times lower than estragol, measured by analogy disclosed in the Journal of Agr. Food Chem., Vol. 19, No. 6, 1971, 1049-1056.

A particularly preferred composition according to the invention may comprise a compound of formula (I) selected from 1-Cyclopropylmethyl-4-methoxy-benzene, 4-Cyclopropylmethyl-2-methoxy-phenol, 4-Cyclopropylmethyl-1,2-dimethoxy-benzene, 2-Methoxy-4-(2-methyl-cyclopropyl)-phenol, 1-Cyclobutylmethyl-4-methoxy-benzene and 1-Cyclopentylmethyl-4-methoxy-benzne. A most preferred composition comprises 1-Cyclopropylmethyl-4-methoxy-benzene.

Some of the compounds of formula (I) are novel, thus, the invention provides in another of its aspects a compound of formula (I) wherein, $R^1$ is hydrogen, OH, or alkoxy having 1 to 3 carbon atoms, $R^2$ is hydrogen, OH, or alkoxy having 1 to 3 carbon atoms, with the proviso that compounds of formula (I) wherein, i) $R^1$, $R^2$ is hydrogen, ii) $R^1$ is hydrogen and $R^2$ is methoxy, iii) $R^1$ is hydrogen and $R^2$ is hydroxy are excluded, or $R^1$ and $R^2$ taken together is a divalent radical —O—$CH_2$—O—, $R^3$ is hydrogen, $R^4$ is hydrogen, or $R^3$ and $R^4$ taken together is a divalent radical —$CH_2$— which forms a cycloalkane ring together with the carbon atoms to which it is attached, $R^5$ is hydrogen, $R^6$ is hydrogen, or $R^5$ and $R^6$ taken together is a divalent radical —$CH_2$— which forms a cycloalkane ring together with the carbon atoms to which it is attached, and wherein at least one cycloalkane ring is present.

Particularly preferred compounds of formula (I) are 4-Cyclopropylmethyl-2-methoxy-phenol, 4-Cyclopropylmethyl-1,2-dimethoxy-benzene and 2-Methoxy-4-(2-methyl-cyclopropyl)-phenol.

The compounds of formula (I) may be synthesised from commonly available starting materials and reagents according to synthetic protocols known in the art. Benzene-cyclopropylmethyl compounds of the formula (I) (i.e. $R^5$ and $R^6$ together=—$CH_2$—) may be synthesised from the corresponding (2-propenyl)-benzene, e.g. 1-methoxy-4-(2-propenyl)-benzene, and methylenebromide in the presence of diethylether and zinc powder and copper chloride according to standard synthetic protocols known in the art.

Benzene-(2-alkyl-cyclopropyl) compounds of the formula (I) (i.e. $R^3$ and $R^4$ together=—$CH_2$—), may be synthesised from the corresponding (1-propenyl)-benzene, e.g. 1-methoxy-4-(1-propenyl)-benzene using the reagents described above according to an analogous synthetic protocol.

Benzene-cycloalkyl-methyl compounds of the formula (I) (i.e. $R^5$ and $R^6$ together=$(CH_2)_3$), may be synthesised from the corresponding benzene, e.g. 1,2-Methylendioxy-benzene, and the corresponding carboxylic acid, e.g. cyclopentylcarboxylic acid, followed by reduction of the intermediate ketones, e.g. benzo[1.3]dioxol-5-yl-cyclopentyl-methanone.

Benzene-alkyl-cycloalkyl compounds of the formula (I) (i.e. $R^3$ and $R^4$ together=$(CH_2)_2$) may be synthesised by analogy to those methods disclosed in J. Organomet. Chem. (1986), 302(1), 5-17, which is hereby incorporated by reference.

Compounds of formula (I) may be used alone or as a mixture in a composition according to the present invention. In addition, the compounds may be used in combination with other known flavourant or odourant molecules selected from the extensive range of natural and synthetic molecules currently available and/or in admixture with one or more ingredients or excipients conventionally used in conjugation with odourants or flavourants in fragrance or flavour compositions, for example carrier materials, and other auxiliary agents commonly used in the art.

In one embodiment, the compounds of formula (I) may be used in fragrance applications, e.g. in any field of fine and functionary perfumery, such as perfumes, household products, laundry products, body care products and cosmetics. The high diffusion and substantivity of compounds of formula (I) is well perceived on fabrics washed with detergent or treated with a softener comprising them. The typical spicy anisic odour is already perceived on wet fabric and lingers for long periods, e.g. 2-4 days on the dry fabric.

In another embodiment, the compounds of formula (I) may be used in flavour applications and are useful in modifying for example, spicy flavours and seasonings for condiments and meats. They may be used in aromatic, herbal and spicy flavourings, heavy fruit flavours (e.g. raisin, prune) and in flavours for Root beer. The compounds of formula (I) are also well suited for mouthwash applications.

In flavourant applications, the compounds of the formula (I) may be present in compositions in amounts ranging from 0.001 to 1000 mg/kg, more preferably from 0.05 to 500 mg/kg.

When used in fragrance applications, compounds of the formula (I) can be employed in wide ranging amounts depending upon the specific application. For example, from about 0.001 to about 10 weight percent. One application may be a fabric softener comprising about 0.001 to 0.05 weight percent. An other application may an alcoholic solution comprising about 0.1 to 10 weight percent. The preferred concentrations vary between about 0.1 and 5 weight percent. However, the values should not be limiting on the present invention, since the experienced perfumer may also achieve effects with even lower concentrations or may create novel accords with even higher amounts.

There now follows a series of examples that illustrate the invention.

EXAMPLE 1

1-Cyclopropylmethyl-4-methoxy-benzene $CH_2Br_2$ (220 g) was added to a slurry of zinc powder (340 g) and CuCl (54 g) in diethyl ether (450 ml). The reaction was started by the addition of acetyl chloride (8 g). The reaction mixture was heated to 45° C. and a solution of estragol (192 g) in ether (150 ml) was added during 25 minutes. Additional $CH_2Br_2$ (456 g) dissolved in ether (150 ml) was dropped into the grey-red suspension during 45 minutes. Afterwards, the mixture was stirred at 50° C. for 12 hours. The suspension was cooled to room temperature and MTBE (900 ml) was added. The mixture was filtered through celite, and the filtrate was washed with saturated $NH_4Cl$, water, saturated $NaHCO_3$ and brine, dried ($MgSO_4$) and concentrated in vacuo. The residue was distilled (b.p. 90-95° C./0.1 Torr) to yield 97.5 g (46%) of a colorless oil, which was found to have the following characteristics, NMR and MS spectra.

$^1$H-NMR (400 MHz, $CDCl_3$): 7.00 (d, J=6.6 Hz, 2H, Ar—H), 6.66 (d, J=6.6 Hz, 2H, Ar—H), 3.61 (s, 3H, $OCH_3$), 2.31 (d, J=6.8 Hz, 2H, Ar—$CH_2$), 0.84-0.74 (m, 1H, Ar—$CH_2CH$), 0.39-0.28 (m, 2H, $CH_2CH(CHaHb)_2$), 0.06-(−0.06) (m, 2H, $CH_2CH(CHaCHb)_2$) ppm. GC/MS (EI): 162 ($M^+$, 40), 147 (11), 134 (34), 121 (100), 91 (26), 77 (15), 65 (10).

The compound has useful odourant properties having an anisic, estragol, anethole, cresolic, strong odor.

EXAMPLE 2 TO 6

5-Cyclopropylmethyl-benzo[1,3]dioxole (A); 4-Cyclopropylmethyl-2-methoxy-phenol (B); 4-Cyclopropylmethyl-1,2-dimethoxy-benzene (C); 2-Methoxy-4-(2-methyl-cyclopropyl)-phenol (D) and 5-(2-methyl-cyclopropyl)-benzo[1,3]dioxole (E) were synthesised by reacting the corresponding propenyl benzene in a procedure analogous to that of Example 1.

Compound (A)

$^1$H-NMR (400 MHz, $CDCl_3$): 6.60-6.50 (m, 3H, Ar—H), 5.74 (s, 2H, $OCH_2O$), 2.29 (d, J=8 Hz, Ar—$CH_2$), 0.81-0.72 (m, 1H, Ar—$CH_2CH$), 0.40-0.28 (m, 2H, $CH_2CH(CHaHb)_2$), 0.08-(−0.06) (m, 2H, $CH_2CH(CHaCHb)_2$). GC/MS (EI): 176 ($M^+$, 42), 148 (32), 135 (100), 115 (8), 89 (10), 77 (23), 51 (12). IR (atr): 3001 w, 2890w, 1503m, 1488s, 1441m, 1248s, 1039s, 809m $cm^{-1}$.

The compound has useful odourant properties having fruity, coriander, anisic, estragol, pear, hesperidic, verdyle odor.

Compound (B)

$^1$H-NMR (200 MHz, $CDCl_3$): 6.69-6.55 (m, 3H, Ar—H), 5.38 (s, 1H, O—H), 3.68 (s, 3H, O—$CH_3$), 2.29 (d, J=7.5 Hz, 2H, Ar—$CH_2$), 0.87-0.67 (m, 1H, Ar—$CH_2CH$), 0.37-0.28 (m, 2H, $CH_2CH(CHaHb)_2$), 0.04-(−0.04) (m, 2H, $CH_2CH(CHaCHb)_2$). GC/MS (EI): 178 ($M^+$, 37), 150 (18), 137 (100), 122 (14), 107 (12), 91 (12), 77 (15), 51 (10). IR (neat): 3527s, 3001m, 2913w, 1605m, 1514s, 1423m, 1269s, 1234m, 1150m, 1035m, 816m $cm^{-1}$.

The compound has useful odourant properties having spicy, eugenol, isoeugenol, smokey odour.

Compound (C)

$^1$H-NMR (200 MHz, $CDCl_3$): 6.61 (bs, 3H, Ar—H), 3.68 (s, 3H, $(O—CH_3)_a$), 3.66 (s, 3H, $(O—CH_3)_b$), 2.31 (d, J=7.0 Hz, Ar—$CH_2$), 0.88-0.68 (m, 1H, Ar—$CH_2CH$), 0.37-0.27 (m, 2H, $CH_2CH(CHaHb)_2$), 0.04-(−0.04) (m, 2H, $CH_2CH(CHaCHb)_2$). GC/MS (EI): 192 ($M^+$, 44), 177 (8), 164 (10), 161 (12), 151 (100), 136 (13), 107 (14), 91 (22), 77 (18), 51 (10). IR (neat): 3076w, 3000m, 2834m, 1590m, 1515s, 1464m, 1263s, 1236m, 1031m $cm^{-1}$.

The compound has useful odourant properties having spicy, clove, methyl-eugenol, dry, linear odour.

Compound (D)

Two isomers in a ratio of 6:1: $^1$H-NMR (200 MHz, $CDCl_3$): 6.85-6.52 (m, 3H, Ar—H), 5.50/5.46 (2s, 1H, O—H), 3.85/3.86 (2s, 3H, O—$CH_3$), 1.56-0.44 (m, 4H), 1.17/0.28 (2d, J=6.5 Hz, CH—$CH_3$) ppm. GC/MS (EI), main isomer: 178 ($M^+$, 82), 163 (32), 147 (23), 137 (15), 131 (100), 117 (18), 103 (45), 91 (26), 77 (20), 65 (10), 55(9). IR (neat):

3523broad, 3000m, 2951m, 2867w, 1604w, 1517s, 1465m, 1263s, 1234s, 1034m, 781w cm$^{-1}$.

The compound has useful odourant properties having eugenol, spicy, peppery, phenolic, thymol odour.

Compound (E)

Two isomers in a ratio of 4:1: $^1$H-NMR (200 MHz, $CDCl_3$): 6.75-6.50 (m, 3H, Ar—H), 5.92/5.88 (2s, 2H, $OCH_2O$), 1.58-0.42 (m, 4H), 1.16/0.77 (2s, J=6.5 Hz, 3H, CH—$CH_3$) ppm. GC/MS (EI), main isomer: 176 ($M^+$, 85), 161 (32), 145 (15), 131 (100), 117 (27), 103 (66), 91 (16), 77 (26), 63 (12), 51 (11). IR (neat): 3000m, 2952m, 1894m, 1503s, 1491s, 1440m, 1254s, 1236s, 1213m, 1041s, 937m, 809m cm$^{-1}$.

The compound has useful odourant properties having estragon, anisic, spicy, animalic odour.

EXAMPLE 7

1-Cyclobutylmethyl-4-methoxy-benzene (F)

A. Cyclobutyl-(4-methoxy-phenyl)-methanone (G)

A solution of $AlCl_3$ (13.4 g) in nitroethane (25 ml) was added to a solution of cyclobutane carboxylic acid (10.0 g) and anisole (10.8 g) in nitroethane (75 ml) at 10° C. The mixture was stirred for 5 hours at room temperature, was than poured on ice and extracted with MTBE. The organic phase was washed with aqueous sodium hydroxide, water and brine, dried ($MgSO_4$) and concentrated in vacuo. The essentially clean ketone (10.8 g) was used in the next step.

B. 1-Cyclobutylmethyl-4-methoxy-benzene (F)

A mixture of compound (G) (5.00 g), hydrazine hydrate (4.12 g), $K_2CO_3$ (7.00 g) and diethylene glycol (16 ml) were heated to reflux temperature for 1 hour. The condenser was exchanged by a distillation device and the mixture was distilled at 220-230° C. The distillate was extracted with MTBE and the organic phase washed with water and brine, dried ($MgSO_4$) and concentrated in vacuo. The residue was purified by chromatography to yield a colorless oil (4.4 g).

Compound (F)

$^1$H-NMR (400 MHz, $CDCl_3$): 7.04 (d, J=6.8 Hz, 2H, Ar—H), 6.80 (d, J=6.8 Hz, 2H, Ar—H), 3.76 (s, 3H, O—$CH_3$), 2.62 (d, J=7.6 Hz, 2H, Ar—$CH_2$CH), 2.51 (sept. J=7.6 Hz, 1H, Ar $CH_2$CH), 2.06-1.64 (m, 6H, Ar—$CH_2$CH ($CH_2$)$_3$) ppm. GCIMS (EI): 176 ($M^+$, 26), 148 (29), 147 (30), 121 (100), 91 (10), 77 (10), 51 (5). IR (atr): 2953m, 2834w, 1612m, 1511s, 1244s, 1176m, 1038m cm$^{-1}$.

The compound has useful odourant properties having anisic, spicy, slightly cuminic, fresh odour.

Compound (G)

$^1$H-NMR (400 MHz, $CDCl_3$): 7.87 (d, J=6.8 Hz, 2H, Ar—H), 6.92 (d, J=6.8 Hz, 2H, Ar—H), 3.95 (quint. J=8.4 Hz, Ar—COCH), 3.85 (s, 3H, O—$CH_3$), 2.45-1.84 (m, 6H, Ar—COCH($CH_2$)$_3$) ppm.

EXAMPLE 8

1-Cyclopentylmethyl-4-methoxy-benzene

This compound was prepared in a procedure analogous to that of Example 7.

$^1$H-NMR (400 MHz, $CDCl_3$): 7.07 (d, J=6.8 Hz, 2H, Ar—H), 6.81 (d, J=6.8 Hz, 2H, Ar—H), 3.77 (s, 3H, O—$CH_3$), 2.54 (d, J=7.6 Hz, 2H, Ar—$CH_2$CH), 2.05 (sept. J=7.6 Hz, 1H, Ar $CH_2$CH), 1.73-1.46 (m, 6H), 1.21-1.12 (m, 2H) ppm. GC/MS (EI): 190 ($M^+$, 12), 121 (100), 91 (6), 77 (6), 41 (5). IR (atr): 2949m, 2866w, 1611m, 1511s, 1244s, 1176m, 1038m cm$^{-1}$.

The compound has useful odourant properties having anisic, spicy, slightly cuminic, herbaceous odour.

EXAMPLE 7

A fougère spicy aromatic masculine fragrance was made with the following ingredients

| | parts per weight |
|---|---|
| Cedryl acetate | 46.0 |
| Vetivenyl acetate extra | 69.0 |
| Cinnamic alcohol | 11.0 |
| Phenyl ethyl alcohol | 38.0 |
| Hexyl cinnamic aldehyde | 46.0 |
| Badiane ess. China | 6.0 |
| Bergamote ess. abergapt orpur | 69.0 |
| Cedarwood ess. Atlas | 15.0 |
| Castoreum artess resin 246 IFRA 10% in DEP | 23.0 |
| Ciste labdanum ess esp rb 10% in DEP | 12.0 |
| Citron ess. Italy orpur | 46.0 |
| Coumarine pure krist. | 34.0 |
| Damascenone 10% in DEP | 3.0 |
| Dipropylene glycol | 3.0 |
| Eugenol pure | 108.0 |
| Evemyl 10% in DEP | 38.0 |
| Geraniol extra | 15.0 |
| Geranium ess. Africa | 12.0 |
| Heliotropine krist. | 20.0 |
| Hydroxycitronellal synth. | 62.0 |
| Isoraldeine 40 | 23.0 |
| Lavandine grosso ess orpur | 31.0 |
| Lilial | 46.0 |
| Linalool synth. | 108.0 |
| Lindenol | 5.0 |
| Litsea cubeba ess. | 15.0 |
| Menthe Crepure ess. USA | 3.0 |
| Musk Ketone | 26.0 |
| Patchouli ess. | 34.0 |
| Pyralone 10% in DEP | 25.0 |
| 1-Cyclopropylmethyl-4-methoxy-benzene (Example 1) | 8.0 |
| | 1000 |

In this fougère type spicy aromatic fragrance, 1-cyclopropylmethyl-4-methoxy-benzene blends excellently with the anisic and spicy notes of the fragrance. Compared to a similar composition containing 10.0 parts of estragol instead of 1-cyclopropylmethyl-4-methoxy-benzene, the above fragrance has more character, is fresher and blends much better with the minty note of the top but also with the animalic notes of the dry down.

The invention claimed is:

1. A fragrance or flavour composition comprising 1-cyclopropylmethyl-4-methoxy-benzene and provides spicy and anisic odor notes to the composition.

2. A fragranced product comprising 1-cyclopropylmethyl-4-methoxy-benzene in an amount ranging from 0.001% to 10%.

3. A flavoured product comprising 1-cyclopropylmethyl-4-methoxybenzene in an amount ranging from 0.001 to 1000 mg/kg.

4. A method of improving a flavour or fragrance composition comprising the step of adding thereto 1-cyclopropylmethyl-4-methoxy-benzene, wherein the 1-cyclopropylmethyl-4-methoxy-benzene provides spicy and anisic odor notes to the composition.

* * * * *